United States Patent [19]
Bousquet

[11] Patent Number: 5,149,713
[45] Date of Patent: Sep. 22, 1992

[54] USE OF BACLOFEN FOR THE TREATMENT OF ANGINA PECTORIS

[75] Inventor: Pascal-Pierre Bousquet, Strasbourg, France

[73] Assignee: Adir et Compagnie

[21] Appl. No.: 704,302

[22] Filed: May 22, 1991

[30] Foreign Application Priority Data

May 23, 1990 [FR] France .................. 90 06437

[51] Int. Cl.$^5$ .......................................... A61K 31/195
[52] U.S. Cl. ................................................ 514/567
[58] Field of Search ...................................... 514/567

[56] References Cited

U.S. PATENT DOCUMENTS

| | | | |
|---|---|---|---|
| 4,084,000 | 4/1978 | Fuxe | 514/567 |
| 4,126,684 | 11/1978 | Robson et al. | 514/567 |
| 4,156,013 | 5/1979 | Bruinvels et al. | 514/567 |
| 5,006,560 | 4/1991 | Kreutner et al. | 514/567 |

OTHER PUBLICATIONS

Chahl, et al., Br. J. Pharmacol. 1980, 69 (4), 631–637.
Page 136 of The Merck Index, Tenth Edition (1983).
Craig et al. *Modern Pharmacology* (1st ed., 1982) pp. 286–291.
Chemical Abstracts 98(9):65227 (1982) Bousquet et al.
Chemical Abstracts 94(1): 211 (1981) Chahl et al.

*Primary Examiner*—Frederick E. Waddell
*Assistant Examiner*—Raymond J. Henley, III

[57] ABSTRACT

The invention relates to the use of baclofen for the treatment of angina pectoris.

1 Claim, No Drawings

USE OF BACLOFEN FOR THE TREATMENT OF ANGINA PECTORIS

The present invention relates to the use of baclofen, its optical isomers and its physiologically acceptable salts for obtaining medicaments for the treatment of angina pectoris. Baclofen, the compound of the formula I:

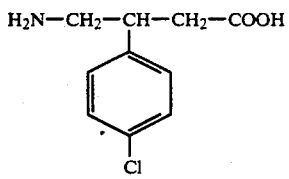

or 4-amino-3-(4-chlorophenyl)-butyric acid, is a compound described in Swiss Pat. No. 449,046 (1968).

Baclofen, which has a muscle-relaxant activity, is used in therapeutics as an antispastic agent and especially in the spastic contracture of multiple sclerosis, medullary disorders or spastic contracture of cerebral origin. (Goodman and Gilman's "The pharmacological basis of therapeutics" 7th Ed. Macmillan Publishing Company 1985 p. 487.)

It is also known that pharmaceutical compositions containing baclofen in association with other medicaments can be used in the symptomatic treatment of multiple sclerosis (JP Patent 01319466) or disorders of the striated musculature (EP 205.492).

Baclofen, when administered in association with narcotics or barbiturates, reduces the risks of dependence or intoxication which may arise from the use of such medicaments (U.S. Pat. No. 4126684).

The association of baclofen with anxiolytics can be useful in treatment against anxiety (FR Patents 249 3703 and 239 3577).

It is also known that, when administered in conjunction with an antihypertensive, baclofen increases the reduction in blood pressure. Baclofen can accordingly be used in association with different antihypertensives for the treatment of hypertension. (GB Patent 154 7609.)

The Applicants have now found that baclofen has valuable pharmacological properties that can be used in obtaining medicaments for the treatment of angina pectoris.

Pharmacological tests have shown that baclofen is an antianginal substance because it prevents an increase in the oxygen requirement in situations triggering angina pectoris attacks, without depressing the basic functioning of the heart. In the case of humans, these situations are physical effort and stress (Braunwald "Heart Disease, A textbook of cardiovascular medicine", ED Saunders W.B (1980) pp. 1387-1389).

The physiopathological bases of the primary therapy of angina pectoris (that is to say, preventing the attack) consist in a development of the following therapeutic strategies:

an increase in the supply of oxygen to the heart by vasodilation of the coronary vascular bed, (Parratt, J.R., Pharmacological approaches to the therapy of angina; Adv. Drug Res. (1974) 8 pp. 103-134)

a reduction in the consumption of oxygen by the myocardium, in particular a reduction in the increase in requirement in situations triggering the angina pectoris attack (Sonnenblick et al., Am. J. Cardiol. (1968) 22 pp. 328-341)

improved distribution of oxygen to the endocardium.

As has been noted hereinbefore, baclofen reduces oxygen requirement.

At least two large families of medicaments already in existence come into this category: beta-blockers and calcium-blocking agents. All, however, affect the basic functioning of the heart, from the point of view of both its contractile force (inotropism) and its contractile rhythm (chronotropism), to such an extent that they are all potentially cardiodepressants and/or arrhythmogenics. Baclofen also comes into this category but, according to the results of animal experiments, it does not depress the basic functioning of the heart, neither from the point of view of the contractile force nor from the point of view of the contractile frequency.

The compound of the formula I is an amphoteric compound of rather basic nature and can accordingly be converted into an addition salt with a pharmaceutically acceptable acid. The addition salts of the compound of the formula I also form part of the present invention. Hydrochloric acid, sulphuric acid, hydrobromic acid, phosphoric acid, etc. may be mentioned as acids.

The invention extends also to pharmaceutical compositions that can be used in the treatment of angina pectoris and contain as active ingredient the compound of the formula I or one of its salts with a pharmaceutically compatible mineral or organic acid, in association with one or more suitable inert excipients. The compound of the formula I or one of its addition salts may also be associated with other compounds used in the treatment of angina pectoris, such as, for example, calcium-blocking agents or betablockers.

The antianginal medicaments obtained by using according to the invention the compound of the formula I or its pharmaceutically acceptable salts, are advantageously presented in various forms, such as, for example, tablets, dragees, soft gelatin capsules, glossettes or other galenical preparations suitable for sublingual administration, suppositories, solutions for endobuccal sprays, galenical preparations suitable for percutaneous administration and injectable or drinkable solutions.

The dosage can vary greatly according to the age of the patient, his or her weight, the mode and frequency of administration, the severity and frequency of the patient's angina pectoris attacks and the associated treatments and ranges from 0.5 to 1 mg/kg per dose or per administration.

The following Examples illustrate the invention:

EXAMPLE 1

Effect of baclofen on cardiovascular changes induced by stimulation of the diencephalon: Test No. 1

Within the framework of an experimental study relating to the production of an animal model of the cardiovascular symptoms encountered during stress or physical effort, it was possible to reproduce such symptoms in the anaesthetised animal, in this case the cat, by the electrical stimulation of a specific zone of the diencephalon.

Cats weighing from 1.5 to 3.5 kg (n=4) were anaesthetised using pentobarbital (from 30 to 40 mg/kg administered first i.p., and then from 3 to 5 mg/kg administered i.v.) and then tracheotomised, curarised and ventilated artificially. The various basic haemodynamic parameters were recorded: arterial systolic and diastolic pressures, cardiac frequency, cardiac output. The various haemodynamic indices and parameters were also calculated (mean arterial pressure, dP/dt, double product frequency×pressure).

The core temperature of the animals was maintained at from 37° to 37.5° C. by means of an electric blanket. The animals were placed in a stereotactic apparatus and then the defence area was stimulated electrically by means of an electrode placed in the grey matter, at coordinates $A_6 L_1 H_0$. The stimuli were supplied by a stimulator functioning in monopolar manner: frequency 100 Hz, duration 3 msec., difference in potential 3 to 6 volts.

The positioning of the electrode is considered to be satisfactory when the cardiac output and dP/dt are increased by more than 20%.

The baclofen was administered via the femoral vein. The animals were given 0.5 mg/kg or 1 mg/kg as the case may be. The various parameters were then recorded 15 minutes and 30 minutes after the injection of baclofen.

As shown by the results in Table I, the electrical stimulation of the diencephalon gives rise to an increase in the anaesthetised animal's cardiac frequency, arterial pressure, cardiac output, dP/dt and cardiac work, which accords with the results obtained by Folkow et al. (Acta Physiol Scand. (1968) 72, p. 220) and Kylstra et al. (Acta Physiol. Scand. (1970) 78, p. 386), (J. Pharm. Exp. Ther. (1982), 223 p. 654) and Djojosugito et al. (Acta Physiol. Scand. (1970) 78, p. 376).

It is known that oxygen consumption depends on cardiac work which in turn depends on cardiac frequency and arterial pressure. The consumption of oxygen is estimated by the double product: cardiac frequency×arterial systolic pressure. Stimulation of the area of defence causes a great increase in the myocardial work and therefore in the consumption of oxygen.

The administration of baclofen, although it makes no change whatsoever to the basic haemodynamic parameters, inhibits in an already significant manner certain haemodynamic responses to stimulation of the diencephalon at doses from 0.5 mg/kg and eliminates them completely at a dose of 1 mg/kg ($p < 0.001$).

TABLE I

| | WITHOUT BACLOFEN | | | BACLOFEN 0.5 mg/kg - i.v. | | | BALCLOFEN 1 mg/kg - i.v. | | |
| --- | --- | --- | --- | --- | --- | --- | --- | --- | --- |
| | Base values | Values under stimulation | Δ | Base values | Values under stimulation | Δ | Base values | Values under stimulation | Δ |
| Cf | 155 ± 5.5 | 192.5 ± 4 | +37.5 | 160 ± 3.5 | 172.5 ± 4.2 | +12.5 | 157.5 ± 4.2 | 160 ± 2.2 | +2.5 |
| ASP | 158 ± 2 | 197.5 ± 5.5 | +39.5 | 150 ± 1 | 170 ± 5 | +20 | 152.5 ± 2.2 | 157.5 ± 2.2 | +5 |
| Cf × ASP | 24040 ± 996 | 38100 ± 1790 | +14060 | 23875 ± 446 | 29350 ± 1255 | +5475 | 24000 ± 530 | 24050 ± 469 | +50 |
| MAP | 130.5 ± 2.2 | 169 ± 4.9 | +38.5 | 129 ± 5.6 | 144.5 ± 3.6 | +15.3 | 132.5 ± 2 | 139 ± 3.8 | +6.5 |
| Co | 0.58 ± 0.062 | 0.79 ± 0.06 | +0.21 | 0.59 ± 0.06 | 0.66 ± 0.062 | +0.07 | 0.58 ± 0.062 | 0.60 ± 0.060 | +0.02 |
| dP/dt | 3465 ± 108 | 4400 ± 244 | +925 | 3400 ± 122 | 4150 ± 258 | +750 | 3350 ± 148 | 3425 ± 170 | +75 |

Δ = Difference between the base value and the value under stimulation
Cf = Cardiac frequency (beats per minute)
Co = Cardiac output (l/min)
ASP = Arterial Systolic Pressure (mm Hg)
Cf × ASP = Double product frequency × pressure (beats × mm Hg × min$^{-1}$)
MAP = Mean arterial pressure (mm Hg)
dP/dt = mm Hg × s$^{-1}$

EXAMPLE 2

Effect of baclofen on cardiovascular changes induced by stimulation of the diencephalon: Test No. 2

The procedure used for this study was identical with that used in Example 1. The number of animals used (cats) was 12.

In this study, the cardiac output was not measured. The results contained in Table II confirm the cardioprotective activity of baclofen.

TABLE II

| | WITHOUT BACLOFEN | | | BACLOFEN 0.5 mg/kg - i.v. | | | BALCLOFEN 1 mg/kg - i.v. | | |
| --- | --- | --- | --- | --- | --- | --- | --- | --- | --- |
| | Base values | Values under stimulation | Δ | Base values | Values under stimulation | Δ | Base values | Values under stimulation | Δ |
| Cf | 169 ± 3.5 | 200 ± 5 | +31 | 171 ± 3 | 187 ± 3.5 | +16 | 168 ± 4 | 173 ± 4 | +5 |
| ASP | 152 ± 7 | 194 ± 8 | +42 | 152 ± 5 | 176 ± 5 | +24 | 153 ± 4 | 154 ± 5 | +1 |
| Cf × ASP | 25775 ± 1255 | 38533 ± 2154 | +12758 | 26003 ± 1035 | 32918 ± 1315 | +6915 | 25841 ± 938 | 26245 ± 1189 | +404 |
| MAP | 123 ± 6.5 | 156 ± 7.5 | +33 | 119 ± 2.4 | 138 ± 6 | +19 | 114 ± 4.3 | 122 ± 6 | +8 |
| dP/dt | 3675 ± 222 | 5033 ± 301 | +1358 | 3641 ± 211 | 4750 ± 266 | +1109 | 3566 ± 204 | 3900 ± 213 | +334 |

Δ = Difference between the base value and the value under stimulation
Cf = Cardiac frequency (beats per minute)
ASP = Arterial Systolic Pressure (mm Hg)
Cf × ASP = Double product frequency × pressure (beats × mm Hg × min$^{-1}$)
MAP = Mean arterial pressure (mm Hg)
dP/dt = mm Hg × s$^{-1}$

I claim:

1. A method for the treatment of angina pectoris in a living animal in need of the same, comprising the step of administering to said animal a dose of a compound selected from baclofen, an isomer thereof and a pharmaceutically-acceptable salt thereof, the dose being one-half to one mg/kg.

* * * * *